United States Patent [19]

Wang

[11] Patent Number: 4,939,251

[45] Date of Patent: Jul. 3, 1990

[54] NOVEL SPIROLACTONES

[75] Inventor: Pen C. Wang, Houston, Tex.

[73] Assignee: Shell Oil Company, Houston, Tex.

[21] Appl. No.: 245,618

[22] Filed: Sep. 16, 1988

Related U.S. Application Data

[63] Continuation-in-part of Ser. No. 172,000, Mar. 23, 1988, and a continuation-in-part of Ser. No. 172,052, Mar. 23, 1988.

[51] Int. Cl.$^5$ .................. C07D 291/04; C07D 419/04
[52] U.S. Cl. .................... 540/489; 540/490; 540/491; 540/500; 540/501; 540/502; 540/503; 544/2; 544/5; 544/6; 544/65; 544/66; 544/67; 544/71; 544/183; 544/220; 544/230; 546/16; 546/20; 548/122; 548/123; 548/126; 548/410
[58] Field of Search ............... 564/134; 548/409, 410, 548/122, 123, 126; 525/166; 540/490, 491, 500, 501, 502, 503; 544/2, 5, 6, 65, 220, 230; 546/16, 20

[56] References Cited

U.S. PATENT DOCUMENTS

| | | | |
|---|---|---|---|
| 2,817,646 | 12/1957 | Payne | 564/134 |
| 4,064,086 | 12/1977 | Cowsar et al. | 260/29.2 R |
| 4,584,364 | 4/1986 | Lubowitz et al. | 528/128 |

OTHER PUBLICATIONS

Pariza et al., Synthetic Communications, vol. 13(3), pp. 243–254 (1983).
Knowles et al., J. Appl. Polymer Sci., vol. 10(6), pp. 887–888 (1966).
Cava et al., J. Am. Chem. Soc., 77, 6022 (1955).
Cava et al., J. Am. Chem. Soc., 79, 1706–1709 (1956).

*Primary Examiner*—William R. Dixon, Jr.
*Assistant Examiner*—Miriam Sohn

[57] ABSTRACT

Novel 1-azaspiro[4.4] lactams are produced by reaction of at least one hydroxy-containing primary amino compound with a 4-ketodiacid compound or a 1,6-dioxaspiro[4.4]lactone. Molar excesses of amion compound result in production of spirodilactams, while limited molar quantities of amino compound results in production of a spirolactam-lactone which reacts further with hydroxy-containing primary amino compound or with hydroxy-free primary amino compound to produce a spirodilactam. Certain of the spirolactams are useful as precursors for glycidyloxy derivatives which react with epoxy curing agents to form insoluble thermoset resins while others are useful as curing agents and yet others are converted to glycidyloxy derivatives useful as reactive diluents in epoxy resin applications.

38 Claims, No Drawings

NOVEL SPIROLACTONES

This application is a continuation-in-part of copending U.S. patent application Ser. No. 172,000, allowed filed Mar. 23, 1988 and copending U.S. patent application Ser. No. 172,052, allowed filed Mar. 23, 1988.

FIELD OF THE INVENTION

This invention relates to certain novel spirolactams and to methods for their production. More particularly, it relates to [4.4] spirolactams having a nitrogen in the 1-position of the spiro ring system and having an aza or an oxa moiety in the 6-position of the spiro ring system as a part of a lactam or a lactone group, respectively. Such spirolactams are produced by reaction of at least one hydroxy-containing amino compound and a spirolactam precursor.

BACKGROUND OF THE INVENTION

The reaction of dibasic acids, or the corresponding esters or acid halides, with diamines or diols to produce open chain polyamides or polyesters is well known in the art. Such polymers are typically thermoplastics with an established utility in a number of applications. A commercial example of such an open chain polyamide is the polymer produced by reaction of hexanedioic acid (adipic acid) and hexamethylenediamine known as Nylon 66 and marketed by DuPont.

A second class of polymeric materials is based in part on difunctional monomers having cyclic or in some cases polycyclic structures within the molecule. These monomers are often thermosetting resins which are typically useful in high temperature applications in part because of the cyclic structure which often leads to properties of strength and rigidity at elevated temperature. It would be of advantage to provide a process for the conversion of open chain dicarboxylic acid compounds to novel products of cyclic or polycyclic structure having useful properties and thereby increase the breadth of utility for the dicarboxylic acid compounds.

A class of compounds having a polycyclic structure is the class of spirodilactones represented by 1,6-dioxaspiro[4.4]nonane-2,7-dione. This spirodilactone is known, being prepared, for example, by Pariza et al, Synthetic Communications, Vol. (13) 3, pp. 243-254 (1983). This spirodilactone has demonstrated utility as a curing agent in epoxy resin systems which do not shrink upon curing. This dimensional stability is thought to result from opening of the lactone ring(s) during the curing process. See knowles et al, J. Appl. Polymer Sci., Vol 10 (6), pp. 887-888 (1966). It is generally considered characteristic of the spirodilactone ring system that reaction with active hydrogen compounds tends to produce ring-opened derivatives, as exemplified by the above Pariza et al publication and by Cowsar, U.S. Pat. No. 4,064,086. It would be of advantage to provide a process for converting the spirodilactone ring system into novel functional derivatives while maintaining the spiro ring system.

SUMMARY OF THE INVENTION

This invention relates to novel spirolactam products and to methods for the production thereof. More particularly, the invention relates to novel [4.4] spirolactams having an additional lactam moiety or alternatively a lactone moiety within the spiro ring system. Such spirolactams are produced by reaction of at least one hydroxy-containing primary amino compound with a spirolactam precursor selected from 4-ketodicarboxylic acid compounds or spirodilactones of corresponding ring structure.

DESCRIPTION OF THE INVENTION

The spiro [4.4] lactams of the invention are produced by reaction of at least one hydroxy-containing primary amino compound, i.e., an organic compound having within the molecule a primary amino group (a $-NH_2$ group) and a hydroxyl group (a $-OH$) group), with a spirolactam precursor. In one modification of the invention, the spirolactam precursor is a ketodicarboxylic acid compound having two carbon atoms between the center carbon of the keto group and each carboxy function, i.e., the ketodicarboxylic acid compound is a 4-oxoheptanedioic acid compound. Although a variety of such ketodiacid compounds having a variety of substituents in addition to the oxo moiety and the carboxy groups, the preferred 4-oxoheptanedioic acid compounds have up to 30 carbon atoms inclusive and are represented by the formula

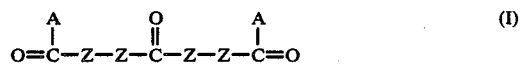

wherein A independently is hydroxy, alkoxy, preferably lower alkoxy of up to 4 carbon atoms, or halo, preferably the middle halogens chloro or bromo; and Z independently is

in which Z' independently is hydrogen, lower alkyl of up to 4 carbon atoms, preferably methyl or halogen, preferably the lower halogen fluoro or chloro, or the Z moieties are such that two adjacent Z groups taken together form a ring system Z" of from 5 to 7 ring atoms, up to two of which are heteroatoms selected from nitrogen, oxygen or sulfur heteroatoms with the remainder of the ring atoms being carbon atoms, there being up to 15 carbon atoms inclusive in each Z", two of which form a connecting group to connect the central carbon atom, in this case the oxo carbon atom, with the carbon atom of a carboxy function. When the Z moieties are taken together to form a ring the ring is cycloaliphatic, aromatic or heterocyclic and is hydrocarbon containing only atoms of carbon besides any heteroatoms or is hydrocarbon additionally containing atoms such as halogen, preferably halogen in the form of inert substituents.

In one embodiment employing the ketodiacid compound spirolactam precursor, each Z moiety is

and the ketodiacid compound spirolactam precursor is an acyclic 4-oxoheptanedioic acid compound. In this embodiment, largely because of a particularly convenient method for preparing the spirolactam precursor, the 4-oxoheptanedioic acid compound preferably has at least one hydrogen on the carbon atom adjacent to each carboxy function, that is, at least one Z' substituent on each carbon atom adjacent to a carboxy function will be hydrogen. Such 4-oxoheptanedioic acid compounds are represented by the formula

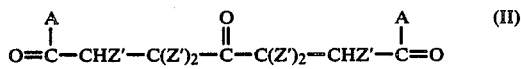

wherein A and Z' have the previously stated meanings. Such 4-oxoheptanedioic acid compounds include 4-oxoheptanedioic acid, dimethyl 4-oxoheptanedioate, 2,6-dimethyl-4-oxoheptanedioic acid, 2,3,5,6-tetramethyl-4-oxoheptanedioyl chloride, 3,5-diethyl-4-oxoheptanedioic acid, di-n-propyl 2,6-di-n-butyl-4-oxoheptanedioate, and 1-carbomethoxy-3,3,5,5-tetramethyl-4-oxohexanoic acid. The preferred ketodiacid compounds of the above formula II are those wherein each Z' is hydrogen or methyl, especially hydrogen, and each A is hydroxy or methoxy, especially hydroxy.

Many of these ketodiacid compounds are known compounds produced by conventional methods but the esters of the above formula II, i.e., the compounds wherein each A is alkoxy, are produced by reaction of formaldehyde and an α,β-ethylenically unsaturated carboxylate ester such as methyl acrylate, ethyl methacrylate, methyl crotonate, methyl ethacrylate and propyl 2,3-dimethyl-butanoate. This reaction is conducted in the presence of a catalyst system which comprises a thiazolium salt and a tertiary amine and produces a dialkyl 4-oxoheptanedioate derivative in good yield. This process is described in greater detail in copending U.S. patent application Ser. No. 171,999, filed Mar. 23, 1988, now U.S. Pat. No. 4,800,231 incorporated herein by reference. Conversion of the esters thereby produced to corresponding free acids or acid halides is by conventional methods as is the interconversion of the acids, esters or acid halides of formula II in general to obtain the 4-oxoheptanedioic acid compounds.

In a second embodiment of the ketodiacid compound spirolactam precursor, the 4-ketodiacid compound incorporates cyclic moieties between the keto group and the carboxy groups, i.e., the two adjacent Z moieties of the above formula I form a cyclic structure. Such cyclic diacid compounds are represented by the formula

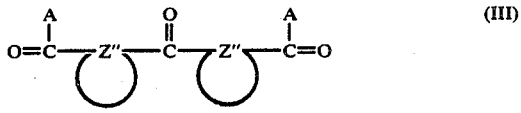

wherein Z'' has the previously stated meaning. Illustrative of these cyclic ketodiacids are di(2-carboxyphenyl) ketone, di(2-carbethoxyphenyl) ketone, di(2-carboxycyclohexyl) ketone, di(2-carbopropoxycyclo-4-pentenyl) ketone, di(2-chlorocarbonylphenyl) ketone, di(2-carboxypyridyl) ketone, 2-carboxyphenyl N-methyl-3-carboxy-2-pyrryl ketone, di(3-carbethoxy-2-morpholyl) ketone and di(3-carbomethoxy-2-naphthyl) ketone. The preferred cyclic ketodiacid compounds of this formula III are those wherein Z'' is a ring system of from 5 to 6 atoms inclusive and up to one nitrogen heteroatom.

Such dicyclic 4-ketodiacid compounds are known compounds or are produced by known methods including the method described by U.S. Pat. No. 1,999,181 or by Cava et al, J. Am. Chem. Soc., 77, 6022(1955).

In yet another embodiment of the ketodiacid compound spirolactam precursor, the ketodiacid incorporates one acylic moiety and one cyclic moiety, e.g., the compounds represented by the formula

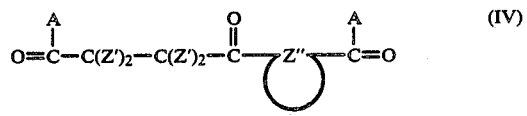

wherein A, Z' and Z'' have the previously stated meanings. Such ketodiacids of one cyclic moiety are illustrated by 3-(2-carboxybenzoyl) propionic acid, 3-(2-carbomethoxy-2-pyridyloyl)-2-ethylpropionic acid, ethyl 3-(2-carbethoxybenzoyl)propionate and 3-(2-carboxy-4-methylbenzoyl) butyrl chloride. The ketodiacid compounds of one cyclic moiety of the formula IV are known compounds or are produced by known methods.

In a second modification of the invention, the spirolactam precursor is a 1,6-dioxaspiro[4.4]nonane-2,7-dione wherein the spiro ring system is unsubstituted except with hydrogen atoms, is substituted with alkyl groups, particularly lower alkyl groups, or halogens, particularly the lower halogens fluoro and chloro, or incorporates cyclic moieties which include the carbon atoms in the 3- and 4-positions and/or the 8- and 9-positions of the spiro ring system. One class of such [4.4] spirolactones is represented by the formula

wherein Z has the previously stated meaning with the understanding that two of the carbon atoms of an Z'' form a connecting group between a carbonyl carbon atom and the center carbon atom, in this case the spiro carbon atom, i.e., the carbon atom common to the two spiro rings.

In the embodiment of the spirodilactone spirolactam precursors of the formula V wherein each Z moiety is C(Z')$_2$, the spirodilactone spirolactam precursor is represented by the formula

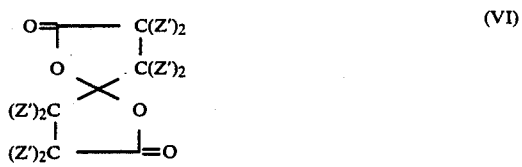

wherein Z' has the previously stated meaning. Illustrative of such spirodilactones are 1,6-dioxaspiro[4.4]nonane-2,7-dione, 3,8-dimethyl-1,6-dioxaspiro[4.4]nonane-2,7-dione, 3,4,8,9-tetramethyl-1,6-dioxaspiro[4.4]nonane-2,7-dione, 4,9-diethyl-1,6-dioxaspiro[4.4]nonane-2,7-dione, 3,3,8,8-tetramethyl-1,6-dioxaspiro[4.4]nonane-2,7-dione, 3,3,4,4,8,8,9,9-octamethyl-1,6-dioxaspiro[4.4]nonane-2,7-dione, 3,4,8,9-tetrafluoro-1,6-dioxaspiro[4.4]nonane-2,7-dione The preferred spirodilactones of the formula VI are those wherein at least one Z' of each Z' -substituted carbon atom is hydrogen. Such compounds are known compounds or are produced by known methods such as the process of the above Pariza et al publication, incorporated herein by reference.

In the embodiment of the spirodilactone spirolactam precursors of the above formula V which incorporate a cyclic moiety as a part of each of the two rings of the spirodilactone ring system, the spirodilactones are represented by the formula

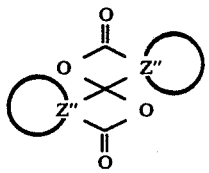 (VII)

wherein Z" has the previously stated meaning. Typical compounds of this formula are 3,4-8,9-dibenzo-1,6-dioxaspiro[4.4]nonane-2,7-dione, 3,4,8,9-cyclopentano 1,6-dioxaspiro[4.4]nonane-2,7-dione 3,4,8,9-di(4-methylbenzo)-1,6-dioxaspiro[4.4]nonane-2,7-dione and 3,4,8,9-di(-pyrido)-1,6-dioxaspiro[4.4]nonane-2,7-dione. These compounds of formula VII are known compounds or are produced by known methods, for example, the process described by Cava et al, J. Am. Chem. Soc., 79, pp. 1706–1709 (1959) or the process disclosed in U.S. Pat. No. 1,999,181.

In a third embodiment of the spirodilactone spirodilactam precursor, one cyclic moiety is fused to one of the spiro rings and the other spiro ring is free of fused ring substituents. Such spirodilactones are represented by the formula

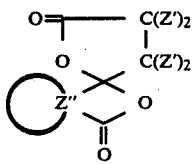 (VIII)

wherein Z' and Z" have the previously stated meanings. Such spirodilactones with a ring fused to one but not both of the spiro rings are represented by 3-methyl-8,9-benzo-1,6-dioxaspiro[4.4]nonane-2,7-dione, 8,9-benzo-1,6-dioxaspiro[4.4]nonane-2,7-dione, and 3,3,4,4-tetramethyl-8,9-(morphino)-1,6-dioxaspiro[4.4]nonane-2,7-dione. Spirodilactones of the above formula VIII are produced by dehydration of the corresponding ketodiacids. For example, 3-(2-carboxyphenyl)propionic acid is dehydrated by application of heat to produce 3,4-benzo-1,6-dioxaspiro[4.4]nonane-2,7-dione.

In general, the preferred spirodilactone spirodilactam precursors are hydrocarbon except for the oxygen atoms of the lactone moieties, particularly those spirodilactones which are free from fused ring substituents (formula VI) or which have a fused ring substituent on each of the spiro rings (formula VII). An especially preferred spirodilactone spirodilactam precursor is 3,4-8,9-dibenzo-1,6-dioxaspiro[4.4]nonane-2,7-dione.

In the process of the invention, the spirodilactam precursor is reacted with at least one hydroxy-containing primary amino compound to produce a [4.4] spirodilactam having at least one nitrogen atom within the spiro ring in a position adjacent to the spiro carbon atom, i.e., the carbon atom common to the two rings, and having a hydroxy-containing substituent attached to each nitrogen atom. The process is adaptable to the production of a variety of spirodilactam products, as is discussed below, depending on the molar ratio of the reactants and the nature of the primary amino compound(s) employed. In one modification, the spirodilactam precursor is reacted with a molar excess, say a two-fold excess, of one or two, preferably one, hydroxy-containing primary amino compounds. Reaction serves to produce a [4.4] spirodilactam having nitrogen atoms in the 1- and the 6-ring positions with the portion of the hydroxy-containing primary amino compound, i.e., the portion remaining when the amino group is excluded, as a substituent on each nitrogen atom. In an alternate modification, a limited molar amount of hydroxy-containing primary amino compound, e.g., no more than one mole per mole of spirodilactam precursor, reacts with the spirolactam precursor to produce a spirolactam-lactone having the oxygen and nitrogen atoms in the 1-and 6-positions of the spiro ring system with the remainder of the hydroxy-containing primary amino compound as a substituent on the nitrogen atom. If desired, the spirolactam-lactone is further reacted with the same or a different hydroxy-containing primary amino compound or alternatively with a primary amino compound free from hydroxy-substitution.

The hydroxy-containing primary amino compound(s) with which the spirolactam precursor reacts as well as any hydroxy-free primary amino compound are of a variety of chemical structures. The precise nature of the group that links the hydroxy group and the amino group, as well as the group to which the primary amino group is attached in the hydroxy-free primary amino compound, is not critical provided that at least three carbon atoms separate the amino group from any hydroxyl group and the group does not provide sufficient steric hindrance to preclude reaction of the amino group with the spirolactam precursor. The linking group is therefore suitably aliphatic or aromatic or mixed aliphatic and aromatic and is hydrocarbyl or is substituted-hydrocarbyl with any atoms other than carbon and hydrogen being present as inert substituents such as middle halo or as divalent portions of the linking groups. In one embodiment the primary amino compound is what is commonly termed a "large molecule" and is an oligomer, prepolymer or polymer which is functionalized to include a primary amino group and optionally a hydroxyl group. A preferred class of primary amino compounds, however, has up to 30 carbon atoms and up to 4 aromatic rings, inclusive, and is represented by the formula $$H_2N-R-X(R)_rG$$ (IX)

wherein R independently has up to 10 carbon atoms, inclusive, and is aromatic or aliphatic, r is 0 or 1, G is hydroxy or hydrogen and X is a direct valence bond, alkylene of up to 8 carbon atoms inclusive, oxo, thio, sulfonyl, keto, dioxyphenylene, e.g.,

2,2-bis(oxyphenyl)propane, e.g.,

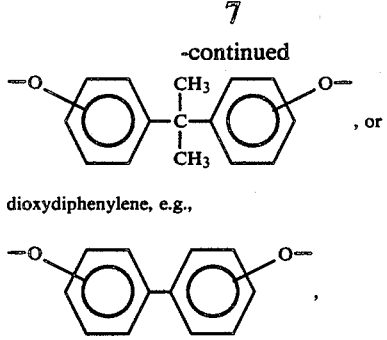

dioxydiphenylene, e.g.,

with the proviso that in at least one of the primary amino compounds of the above formula IX with which the spirodilactam precursor reacts that G is hydroxy, i.e., a compound of the formula $$H_2N-R-X(R)_rOH \quad (X)$$

wherein R, X and r have the previously stated meanings.

Illustrative of the primary amino compounds of the above formula IX wherein G is hydroxy (compounds of the above formula X) are p-aminophenol, 6-aminohexanol, 1-amino-5-hydroxynaphthalene, 4-aminophenyl 3-hydroxyphenyl ether, 2-(3-hydroxyphenylthio)ethylamine, 4-amino-1'-hydroxybiphenyl, 2-hydroxypropyl 4-aminophenyl ketone, m-aminophenol, 1-(4-hydroxyphenyloxy)-3-(3-aminophenyloxy)benzene, 2-(3-hydroxyphenyloxyphenyl)-2-(2-aminophenyloxyphenyl)propane, 5-(4-aminophenyl)-1-pentanol, (4-aminophenyl)(3-hydroxyphenyl)methane, 2-(4-aminophenyl)-2-(4-hydroxyphenyl)propane, 4-amino-3-chlorophenol, 4-amino-o-cresol, 4-(2-aminoethyl)-phenol and 4-aminocyclohexanol.

Illustrative of the compounds of the above formula IX wherein G is hydrogen are those compounds of the formula $$H_2N-R-X(R)_rH \quad (XI)$$

wherein R, X and r have the previously stated meanings. Such hydroxyl-free primary amino compounds include methylamine, 1-octylamine, aniline, 4-aminobiphenyl, 1-naphthyamine, (4-aminophenyl) phenyl ketone, 3-phenylbutyl amine, (4-phenoxy)aniline and phenyl(4-aminophenyl)sulfone.

The compounds wherein all R groups present in the molecule are aromatic are preferred over the primary amino compounds wherein an aliphatic R group is present, especially those primary amino compounds which are otherwise hydrocarbyl and wherein r is 0. The aminophenols are a preferred class of hydroxy-containing primary amino compounds, particularly p-aminophenol. Among hydroxy-free primary amino compounds, the anilines are a preferred class, particularly aniline.

The spirolactam precursor is contacted with at least one hydroxy-containing primary amino compound to produce a [4.4] spirolactam, the nature of which will depend upon the choice of spirodilactam precursor and the ratio of reactants which is employed. When the ratio of reactants is such that the spirolactam precursor is present in a molar quantity of about equal to or greater than the molar quantity of hydroxy-containing primary amino compound, the predominant product is a spirolactam-lactone wherein the amino moiety of the hydroxy-containing primary amino compound has been incorporated into the spiro ring system with the amino nitrogen being located in the ring system in a position adjacent to the spiro carbon atom, the remainder of the hydroxy-containing primary amino compound being present as a substituent on the ring nitrogen atom and a lactone group being present with the non-carbonyl lactone oxygen also present in a ring position adjacent to the spiro carbon atom. In terms of the hydroxy-containing primary amino compound and the spirolactone precursor as described above, the spirolactam-lactone will be represented by the formula

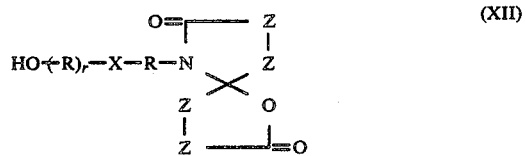

wherein R, r, X and Z have the previously stated meanings. The particular spirolactam precursor to be employed will depend in part upon the particular spirolactam product desired. If the desired spirolactam product, e.g., the spirolactam-lactone of formula XII, has no substituents or one substituent (other than hydrogen) on the ring carbon atoms in the 3- and/or 8-positions, then the choice of spirolactam precursor is not limited except by the presence or absence of additional fused rings. If, however, the desired spirolactam product has two substituents other than hydrogen on the ring carbon atoms in the 3 and/or 8-positions, the spirolactam precursor of the above formula II is not suitable and an alternate spirolactam precursor should be employed.

The identity of the spirolactam-lactone products of the above formula XII will be apparent from the above description of the hydroxy-containing primary amino compound, the spirolactam precursor and the spirolactam-lactone product. By way of specific example, however, from the reaction of p-aminophenol and 4-oxoheptanedioic acid is obtained 1-(4-hydroxyphenyl)-6-oxa-1-azaspiro[4.4]nonane-2,7-dione and from the reaction of 4-aminophenyl 4-hydroxyphenyl ether and 3,4-8,9-dibenzo-1,6-dioxaspiro[4.4]nonane-2,7-dione is obtained 1-[4-(4-hydroxyphenyloxy)phenyl]-3,4-8,9-dibenzo-1,6-dioxaspiro[4.4]nonane-2,7-dione is obtained nonane-2,7-dione.

A second modification of the process of the invention leads to the production of a spirodilactam which, in terms of the spirolactam precursor and the primary amino compounds described above, is represented by the formula

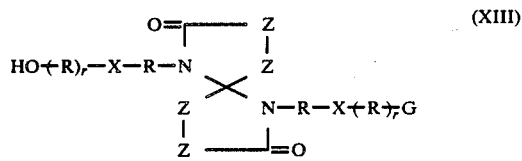

wherein R, r, X, Z and G have the previously stated meanings. Such a spirodilactam is produced by several alternative processes, depending largely upon the particular spirodilactam product desired. In one embodiment, a spirodilactam having a hydroxy-containing substituent on each of the spiro ring nitrogen atoms, e.g., a compound of the above formula XIII, is produced from hydroxy-substituted primary amino compound and spirolactam precursor in one reaction step. In this embodiment, the hydroxy-substituted primary amino compound is employed in a molar quantity in excess of the hydroxy-substituted primary amino compound. To obtain a spirodilactam as the predominant product, the molar quantity of hydroxy-containing primary amino compounds is preferably at least about twice the molar quantity of spirolactam precursor. The quantity of hydroxy-containing primary amino compound may comprise a single hydroxy-containing primary amino compound, in which case a single hydroxy-containing primary amino product of the above formula XIII will be obtained. Alternatively, a mixture of hydroxy-containing primary amino compounds, e.g., two such amino compounds, may be utilized and a spirodilactam containing two different hydroxy-containing spiro ring nitrogen substituents will be obtained as well as lesser amounts of each spirodilactam having the same hydroxy-containing substituent present as derived from each of the hydroxy-containing primary amino compounds employed as reactant.

In order to obtain a spirodilactam in which the hydroxy-containing spiro ring nitrogen substituents are different, a somewhat different two-step process is preferred. Initially, a hydroxy-substituted primary amino compound in limited molar quantity is reacted with the spirolactam precursor to obtain a spirolactam-lactone product of the above formula XII. The spirolactam-lactone, with or without isolation or purification, is then reacted with a second hydroxy-containing primary amino compound to produce a spirodilactam of formula XIII (wherein G is hydroxyl) wherein the hydroxy-containing substituents on the spiro ring nitrogen atoms are different.

The spirodilactams wherein the hydroxy-containing substituents are the same are illustrated by 1,6-di(3-hydroxyphenyl)-1,6-diazaspiro[4.4]-nonane-2,7-dione produced from m-aminophenol and 1,6-dioxaspiro[4.4-]nonane-2,7-dione and by 1,6-di[4-(4-hydroxyphenyl)-phenyl]-3,4-8,9-di(1-aza-1,4-butylidinyl)-1,6-diazaspiro[4.4]nonane-2,7-dione produced from di(3-carboxy-2-pyridyl) ketone and 4-amino-4'-hydroxybiphenyl.

In the embodiment wherein the hydroxy-containing substituents are different, the spirodilactams are illustrated by 1-(4-hydroxyphenyl)-6-(3-hydroxyphenyl)-1,6-diazaspiro[4.4]nonane-2,7-dione produced from p-aminophenol, m-aminophenol and 4-oxoheptanedioic acid. The spirodilactam is produced by reaction of a mixture of the aminophenols with the 4-oxoheptanedioic acid, or by reaction of either of the aminophenols with the acid to produce a spirolactam-lactone, i.e., a 1-(hydroxyphenyl)-6-oxa-1-azaspiro[4.4]nonane-2,7-dione, which reacts subsequently with the other aminophenol to produce the spirodilactam.

In yet another modification of the process of the invention, a spirodilactam having only a single hydroxy-containing substituent is produced by reaction of the spirolactam-lactone of the above formula XII with a hydroxy-free primary amino compound, i.e., the compound of the above formula IX wherein G is hydrogen. The resulting spirodilactam having one hydroxy-containing spiro ring nitrogen substituent and one hydroxy-free spiro ring substituent is of the above formula XIII wherein G is hydrogen. The identity of such spirodilactams of one hydroxy-containing substituent will be apparent from the above description of the reactants and the spirodilactam product. By way of specific illustration, however, 1-(4-hydroxyphenyl)-6-phenyl-1,6-diazaspiro[4.4]nonane-2,7-dione is produced from 1-(4-hydroxyphenyl)-6-oxa-1-azaspiro[4.4]nonane-2,7-dione and aniline and 1-[1-(5-hydroxynaphthyl)]-6-hexyl-1,6-diazaspiro[4.4]nonane-2,7-dione is produced from 1-hexylamine and 1-[-1-(5-hydroxynaphthyl)-6-oxa-1-azaspiro[4.4]-nonane -2,7-dione.

Regardless of the particular reaction of primary amino compound with spirolactam precursor or spirolactam-lactone according to the process of the invention, the reaction preferably takes place in a liquid phase in the presence of an inert reaction diluent which is liquid at reaction temperature and pressure. Preferred reaction diluents are liquid inert polar reaction diluents in which the primary amino compound reactant and the spirolactam precursor or spirolactam-lactone are soluble. Suitable diluents include dialkyl ketones such as methyl ethyl ketone, methyl isobutyl ketone and di-i-propyl ketone; esters such as butyl acetate and methyl 2-ethylhexanoate; ethers including acrylic ethers such as diethyleneglycol diethyl ether and tetraethyleneglycol dimethyl ether as well as cyclic ethers such as dioxane and tetrahydrofuran; sulfur-containing diluents such as sulfolane and dimethyl sulfoxide; and N-alkylamides such as N,N-dimethylacetamide, N,N-dimethylformamide and N-methyl-2-pyrrolidone. The N-alkylamides are a preferred class of reaction diluents, particularly N-methyl-2-pyrrolidone.

The spirolactam precursor or the spirolactam-lactone and the primary amino compound are contacted under reaction conditions in solution in the reaction diluent by conventional methods such as stirring, shaking or refluxing. Suitable reaction temperatures are from about 80° C. to about 250° C., preferably from about 100° C. to about 200° C., depending in part upon the particular reaction diluent employed. Suitable reaction pressures are those sufficient to maintain the reaction mixture in a liquid phase. Typically such pressures are up to about 20 atmospheres but more often are from about 0.8 atmospheres to about 10 atmospheres.

The ratio of the reactants to be employed depends greatly upon the type of product which is desired. To produce a spirodilactam of formula XIII by reaction of a hydroxy-containing primary amino compound and a spirolactam precursor, a molar ratio of amino compound to spirolactam precursor from about 1.5:1 to about 8:1 is satisfactory, although higher ratios are also satisfactory. Molar ratios of amino compound to spirolactam precursor from about 1.8:1 to about 3:1 are preferred. To produce a spirolactam-lactone (formula XII) by reaction of a hydroxy-containing primary amino compound, a limited quantity of the amino compound is employed. Molar ratios of hydroxy-containing primary amino compound to spirolactam precursor from about 0.5:1 to about 1.3:1 are suitable with molar ratios from about 0.8:1 to about 1.1:1 being preferred. Reaction of the spirolactam-lactone and primary amino compound to produce a spirodilactam typically employs a molar quantity of primary amino compound of at least one mole of the primary amino per mole of spirolactam-lactone. Molar amounts of primary amino compound from about 1 mole to about 3 moles per mole of spirolactam-lactone are preferred.

Subsequent to reaction, the spirolactam product is recovered, if desired, by conventional methods such as precipitation, selective extraction or distillation. If, however, the initial spirolactam product is a spirolactam-lactone product to be employed in a subsequent conversion to a spirodilactam, it is not generally necessary to separate the initial product and the reaction to produce spirodilactam is often conducted with isolating the spirolactam-lactone.

The hydroxy-substituted spirolactams find utility as precursors of resin materials. The spirodilactams with two hydroxy-containing substituents are particularly useful because of the structural feature of having a polycyclic center portion with hydroxyl groups on the outer portions of the molecule. By way of specific illustration, such spirodilactams are reacted with epichlorohydrin to produce corresponding di(glycidyloxy)-substituted spirodilactams which are cured with conventional epoxy curing agents to produce insoluble thermoset resins having good properties of strength and rigidity with a desirable glass transition temperature. The production of the diglycidyl derivatives of the hydroxy-substituted spirodilactams is described more fully and is claimed in copending U.S. patent application Ser. Nos. 172,054, filed Mar. 23, 1988 and 245,434, filed Sept. 16, 1988 incorporated herein by reference. The spirolactam-lactones are useful as curing agents for epoxy resins and either the spirolactam-lactone or the monohydroxy-substituted spirodilactone (formula XIII wherein G is hydrogen) are converted to a glycidyloxy derivative by the method described above which is useful as a reactive diluent in epoxy resin applications.

The invention is further illustrated by the following Illustrative Embodiments which should not be construed as limiting.

ILLUSTRATIVE EMBODIMENT I

A mixture of 25 g (0.16 mols) of 1,6-dioxaspiro[4.4-]nonane-2,7-dione and 34.9 g (0.32 mole) of p-aminophenol and 100 ml of N,N-dimethylacetamide was placed in a 500 ml round-bottomed flask equipped with a mechanical stirrer and a condenser. The mixture was heated to 165° C. with stirring and refluxed for 12 hours. After cooling, the N,N-dimethylacetamide was removed under reduced pressure and methanol was added to precipitate the product. The precipitated product was recovered by filtration, washed several times with methanol and dried in a vacuum oven at 150° C. for 24 hours. The product had a melting point of 320° C. and the nuclear resonance spectra were consistent with the structure 1,6-di(4-hydroxyphenyl)-1,6-diazaspiro[4.4]nonane-2,7-dione.

ILLUSTRATIVE EMBODIMENT II

The procedure of Illustrative Embodiment I was repeated employing 34.9 g (0.032 mole) of m-aminophenol in place of the p-aminophenol of Illustrative Embodiment I. The product had a melting point of 270° C. and the nuclear magnetic resonance spectra were consistent with the structure 1,6-di(3-hydroxyphenyl)-1,6-diazaspiro[4.4]nonane-2,7-dione.

ILLUSTRATIVE EMBODIMENT III

A mixture of 25 g (0.14 mole) of 4-oxoheptanedioic acid, 31.34 g (0.28 mole) of p-aminophenol and 100 ml of N,N-dimethylacetamide was placed in a 500 ml round-bottomed flask equipped with a mechanical stirrer and condenser. While being stirred, the mixture was warmed to 165° C. and refluxed for 12 hours. After cooling, the N,N-dimethylacetamide was removed under reduced pressure and methanol was added to precipitate the product. The precipitated product was washed several times with methanol and then dried it in a vacuum oven at 150° C. for 24 hours. The product had a melting point of 320° C. and the nuclear magnetic resonance spectra were consistent with the structure 1,6-di(4-hydroxyphenyl)-1,6-diazaspiro[4.4]nonane-2,7-dione.

ILLUSTRATIVE EMBODIMENT IV

The procedure of Illustrative Embodiment III was repeated except that 31.34 g of m-aminophenol was employed in place of the p-aminophenol of Illustrative Embodiment III. The product had a melting point of 270° C. and the nuclear magnetic resonance spectra were consistent with the structure 1,6-di(3-hydroxyphenyl)-1,6-diazaspiro[4.4]nonane-2,7-dione.

ILLUSTRATIVE EMBODIMENT V

A mixture of 100 g (0.574 mole) of 4-oxoheptanedioic acid, 260.7 g (1.148 mole) of 2-(4-aminophenyl)-2-(4-hydroxyphenyl)propane and 250 ml of N-methyl-2-pyrrolidone was placed in a 3 liter round-bottomed flask equipped with a mechanical stirrer and a condenser. While being stirred, the mixture was warmed to 160° C. and maintained at that temperature for 72 hours. After cooling, the N-methyl-2-pyrrolidone was removed under reduced pressure and methanol was added to precipitate the product. The product was washed several times with methanol and then dried in a vacuum oven at 80°–90° C. for 24 hours. A nuclear magnetic resonance analysis of the product indicated a mixture of a major amount of 1,6-di[4-(4-hydroxyphenylisopropyl)phenyl]-1,6-diazaspiro[4.4]nonane-2,7-dione and a minor amount of 1-[4-(4-hydroxyphenylisopropyl)-phenyl]-6-oxa-1-azaspiro[4.4]nonane-2,7-dione.

ILLUSTRATIVE EMBODIMENT VI

The procedure of Illustrative Embodiment V was repeated except that 90 g of 1,6-dioxaspiro[4.4]nonane-2,7-dione was employed instead of the 4-oxoheptanedioic acid. A nuclear magnetic resonance analysis indicated the formation of the same reaction product mixture as found in Illustrative Embodiment V.

ILLUSTRATIVE EMBODIMENT VII

A mixture of 13.6 g (0.05 mole) of di(2-carboxyphenyl) ketone, 10.99 g (0.1 mole) of 4-aminophenol and 50 ml of N-methyl-2-pyrrolidone was placed in a 500 ml round-bottomed flask equipped with a mechanical stirrer and a condenser. While being stirred, the mixture was warmed to 190° C. and maintained at that temperature for 7 days. After cooling, the N-methyl-2-pyrrolidone was removed under reduced pressure and methanol was added to precipitate the product. The precipitated product was washed several times with methanol and dried in a vacuum oven at 150° C. for 24 hours. The product had a melting point above 350° C. and nuclear magnetic resonance spectra of the product was consistent with the structure 1,6-di(4-hydroxyphenyl)-3,4,8,9-dibenzo-1,6-diazaspiro[4.4]nonane-2,7-dione.

What is claimed is:
1. A [4.4]spirolactam product selected from
   (a) a [4.4]spirodilactam wherein the ring nitrogen atoms are in the 1- and the 6- ring positions and each nitrogen is substituted with a hydroxy-containing substituent of up to 30 carbon atoms and up to 4 aromatic rings, inclusive,
   (b) a [4.4]spirodilactam wherein the ring nitrogen atoms are in the 1- and the 6-ring positions, one nitrogen atom is substituted with a hydroxy-con- taining substituent of up to 30 carbon atoms and up to 4 carbon aromatic rings, inclusive, and the other nitrogen is substituted with a hydroxy-free substituent of up to 30 carbon atoms and up to 4 aromatic rings, inclusive, or (c) a [4.4]spirolactam-lactone wherein the lactam nitrogen and the lactone oxygen are in ring positions adjacent to the spiro carbon atom and the nitrogen is substituted with a hydroxy-containing substituent of up to 30 carbon atoms and up to 4 aromatic rings, inclusive.

2. The spirolactam product selected from spirodilactam of the formula

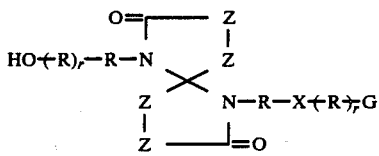

or spirolactam-lactone of the formula

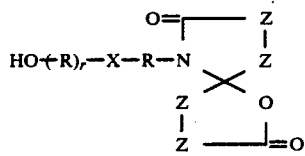

wherein Z is

in which Z' independently is hydrogen or lower alkyl, or such that 2 adjacent Z moieties together form a ring system Z of from 5 to 7 ring atoms, up to two of which are heteroatoms selected from nitrogen, oxygen or sulfur with the remainder of the ring atoms being carbon atoms, there being up to 15 carbon atoms in each Z", two of which form a bridge between carbon atom of a carboxy function and the center carbon atom; R independently is aliphatic or aromatic of up to 10 carbon atoms inclusive; r is 0 or 1; G is hydroxy or hydrogen; and X is a direct valence bond, alkylene of up to 8 carbon atoms inclusive, oxo, thio, sulfonyl, keto, dioxyphenylene, 2,2-bis(oxyphenyl)propane or dioxydiphenylene.

3. The spirodilactam of claim 2 wherein each R is aromatic.

4. The spirodilactam of claim 3 wherein each Z is acyclic.

5. The spirodilactam of claim 4 wherein X is alkylene.

6. The spirodilactam of claim 5 of the formula 1,6-di[4-(4-hydroxyphenylisopropyl)phenyl]-1,6-diazaspiro[4.4]nonane-2,7-dione.

7. The compound of claim 6 of the formula 1,6-di(4-hydroxyphenyl)-1,6-diazaspiro[4.4]nonane-2,7-dione.

8. The compound of claim 6 of the formula 1,6-di(3-hydroxyphenyl)-1,6-diazaspiro[4.4]nonane-2,7-dione.

9. The spirodilactam of claim 3 wherein each Z forms part of a ring system.

10. The spirodilactam of claim 9 of the formula 1,6-di(4-hydroxyphenyl)-3,4,8,9-dibenzo-1,6-diazaspiro nonane-2,7-dione.

11. The spirodilactam of claim 2 wherein G is hydrogen.

12. The compound of claim 11 of the formula 1-(4-hydroxyphenyl)-6-phenyl-1,6-diazaspiro[4.4]nonane-2,7-dione.

13. The spirolactam-lactone of claim 3.

14. The spirolactam-lactone of claim 13 wherein each R is aromatic.

15. The spirolactam-lactone of claim 14 wherein X is a direct valence bond and r is 0.

16. The spirolactam-lactone of claim 15 of the formula 1-(4-hydroxyphenyl)-6-oxo-1-azaspiro[4.4]nonane-2,7-dione.

17. A process for the production of a spirolactam product by reacting a spirolactam precursor selected from a 4-oxoheptanedioic acid compound or a 1,6-dioxaspiro[4.4]nonane-2,7-dione with at least one hydroxy-containing primary amino compound of the formula H$_2$N-R-X(--R)$_r$—OH wherein R independently is aliphatic or aromatic of up to 10 carbon atoms inclusive, r is 0 or 1, and X is a direct valence bond, alkylene of up to 8 carbon atoms inclusive, oxo, thio, sulfonyl, keto, dioxyphenylene, 2,2-di(oxyphenyl)propane and dioxydiphenylene.

18. The process of claim 17 wherein the spirolactam product is the spirodilactam of the formula

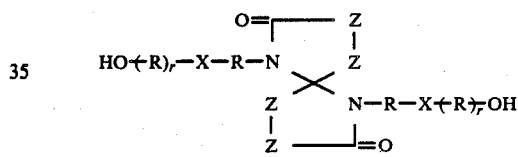

wherein Z independently is

in which Z' independently is hydrogen or lower alkyl, or such that two adjacent Z moieties together form a ring system Z" of from 5 to 7 ring atoms, up to two of which are heteroatoms selected from nitrogen, oxygen or sulfur with the remainder of the ring atoms being carbon, there being up to 15 carbon atoms in each Z", two of which form a bridge between the keto carbon atom and the spiro carbon atom.

19. The process of claim 18 wherein the hydroxy-containing primary amino compound is aminophenol.

20. The process of claim 19 wherein the aminophenol is 4-aminophenol.

21. The process of claim 20 wherein the spirolactam precursor is a 4-oxoheptanedioic acid compound.

22. The process of claim 21 wherein the 4-oxoheptanedioic acid compound is 4-oxoheptanedioic acid.

23. The process of claim 20 wherein the spirolactam precursor is a 1,6-diazaspiro[4.4]nonane-2,7-dione.

24. The process of claim 23 wherein the 1,6-dioxaspiro[4.4]-nonane-2,7-dione is 1,6-dioxaspiro[4.4]nonane-2,7-dione.

25. The process of claim 23 wherein the 1,6-dioxaspiro[4.4]-nonane-2,7-dione is 3,4,8,9-dibenzo-1,6-dioxaspiro[4.4]nonane-2,7-dione.

26. The process of claim 17 wherein the spirolactam product is the spirolactam-lactone product of the formula

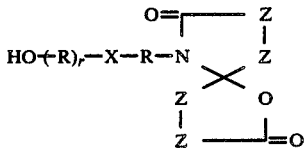

wherein Z independently is

in which Z' independently is hydrogen or lower alkyl, or such that two adjacent Z moieties together form a ring system Z" of from 5 to 7 ring atoms, up to two of which are heteroatoms selected from nitrogen, oxygen or sulfur with the remainder of the ring atoms being carbon atoms, there being up to 15 carbon atoms in each Z", two of which form a bridge between the keto carbon atom and the spiro carbon atom.

27. The process of claim 26 wherein the spirolactam-lactone is further reacted with a primary amino compound of the formula

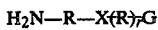

wherein G is hydroxy or hydrogen.

28. The process of claim 27 wherein the amino compound is aniline.

29. The process of claim 26 wherein each Z is acyclic.

30. The process of claim 27 wherein the spirolactam precursor is a 4-oxoheptanedioic acid compound.

31. The process of claim 28 wherein the hydroxy-containing primary amino compound is aminophenol.

32. The process of claim 29 wherein the 4-oxoheptanedioic acid compound is 4-oxoheptanedioic acid.

33. The process of claim 26 wherein the spirolactam precursor is a 1,6-dioxaspiro[4.4]nonane-2,7-dione.

34. The process of claim 31 wherein the 1,6-dioxaspiro[4.4]nonane-2,7-dione is 1,6-dioxaspiro[4.4]nonane-2,7-dione.

35. The process of claim 32 wherein the hydroxy-containing primary amine is aminophenol.

36. The process of claim 33 wherein the aminophenol is 4-aminophenol.

37. The process of claim 31 wherein the 1,6-dioxaspiro[4.4]nonane-2,7-dione is 3,4,8,9-dibenzo-1,6-dioxaspiro[4.4]nonane-2,7-dione.

38. The process of claim 26 wherein the primary amino compound is 4-aminophenol.

* * * * *